United States Patent
Nagahama et al.

(12)

(10) Patent No.: US 6,303,662 B1
(45) Date of Patent: Oct. 16, 2001

(54) MICROEMULSION

(75) Inventors: Tohru Nagahama; Kazuo Hasegawa, both of Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/402,999

(22) PCT Filed: Apr. 17, 1998

(86) PCT No.: PCT/JP98/01763

§ 371 Date: Oct. 15, 1999

§ 102(e) Date: Oct. 15, 1999

(87) PCT Pub. No.: WO98/47486

PCT Pub. Date: Oct. 29, 1998

(30) Foreign Application Priority Data

Apr. 18, 1997 (JP) ................................... 9-101113

(51) Int. Cl.⁷ .................... A01N 37/00; A01N 43/54; A01N 31/00; A61K 31/21; A61K 31/505; A61K 31/045

(52) U.S. Cl. .................... 514/937; 514/513; 514/738; 514/763; 514/267; 514/938; 514/937; 424/400; 424/401

(58) Field of Search .................... 424/401, 400, 424/450; 514/938, 937

(56) References Cited

U.S. PATENT DOCUMENTS

| | | | |
|---|---|---|---|
| 4,407,821 | * | 10/1983 | Mendy ................................. 424/312 |
| 4,572,832 | * | 2/1986 | Kigasawa et al. .................... 424/19 |
| 4,990,340 | * | 2/1991 | Hidaka et al. ........................ 424/449 |
| 5,428,026 | * | 6/1995 | Colarow ................................. 514/78 |
| 5,443,846 | * | 8/1995 | Yoshioka et al. .................... 424/498 |
| 5,993,858 | * | 11/1999 | Crison et al. ........................ 424/490 |
| 6,001,384 | * | 12/1999 | Jeannin ................................ 424/405 |
| 6,063,762 | * | 5/2000 | Hong et al. ............................. 514/11 |
| 6,093,410 | * | 7/2000 | Peffly et al. ......................... 424/401 |
| 6,096,338 | * | 8/2000 | Lacy et al. ........................... 424/455 |
| 6,153,657 | * | 11/2000 | Kisuno et al. ....................... 516/925 |

FOREIGN PATENT DOCUMENTS

| | | |
|---|---|---|
| 63-10717 | 1/1988 | (JP) . |
| 63-126543 | 5/1988 | (JP) . |
| 63-61050 | 11/1988 | (JP) . |
| 1-288330 | 11/1989 | (JP) . |
| 6-57316 | 8/1994 | (JP) . |
| 7-23303 | 3/1995 | (JP) . |

* cited by examiner

Primary Examiner—Dameron L. Jones
Assistant Examiner—Lauren Q. Wells
(74) Attorney, Agent, or Firm—Lurosso & Loud

(57) ABSTRACT

A microemulsion containing (A) a highly polar and fat-soluble oil drug, a highly polar oil and a lowly polar oil, (B) a polyglycerol mono-fatty acid ester and (C) a water-soluble polyhydric alcohol, wherein the amount of (B) is 0.3 to 3 parts by weight based on one part by weight of (A) and the amount of (C) is 0.1 to 3 parts by weight based on one part by weight of the total amount of (A) and (B). The present invention makes it possible to make a microemulsion containing a highly polar and fat-soluble drug which is highly stable.

13 Claims, No Drawings

MICROEMULSION

TECHNICAL FIELD

The present invention relates to a microemulsion containing a highly polar and fat-soluble drug, and more particularly relates to a microemulsion which has a minute particle size and has an enhanced stability of the drugs in aqueous solutions.

BACKGROUND ART

In order to produce a liquid preparation of fat-soluble drugs in the past, there were adopted methods for preparing an aqueous solution by dissolving these drugs in a solubilizing agent such as alcohols or surface active agents. In particular, it is ordinary to use polyoxyethylene hydrogenated castor oils or polyoxyethylene glycol fatty acid esters as a surface active agent in the methods for dissolving the fat-soluble drugs. However, the amount of the fat-soluble drug which can be dissolved by these methods is insufficient, and the internal liquid preparation obtained thereby is uncomfortable in taste.

On the other hand, in order to contain a fat-soluble drug in an aqueous liquid preparation, there is widely used a method wherein the fat-soluble drug is dissolved in an oil and stirred together with an emulsifying agent to give an emulsion, thereby an aqueous phase and an oily phase are completely isolated from each other.

It is known that the stability of emulsions ordinarily increases with decreasing the particle size of emulsions. Japanese Patent Publication Nos. 88-61050-B and 94-57316-B disclose techniques for the preparations of emulsions with minute particles (microemulsion). However, these techniques have a drawback which, when a highly polar and fat-soluble drug is applied thereto, the particle size of the emulsion is increased, and the emulsion becomes unstable by heating, acids and ionic substances.

In addition, Japanese Patent Publication No. 95-23303-B discloses a microemulsion preparation containing a slightly water-soluble drug, however, the microemulsion described in the patent needs vigorous stirring at the time of production thereof, and it is impossible to apply a highly polar and fat-soluble drug thereto.

DISCLOSURE OF THE INVENTION

As a result of extensive researches, the present inventors have found that a highly polar and fat-soluble drug is combined with a mixture of a highly polar oil and a lowly polar oil as an oil for dissolution, a specific amount ratio of a polyglycerol mono-fatty acid ester as an emulsifying agent to the oil and a specific amount of a water-soluble polyhydric alcohol with stirring to give a gel, which is then diluted with water, thereby there is obtained an O/W emulsion having minute particles, thus the present invention has been accomplished.

That is, the present invention is directed to a microemulsion which contains (A) a highly polar and fat-soluble drug, a highly polar oil and a lowly polar oil, (B) a polyglycerol mono-fatty acid ester and (C) a water-soluble polyhydric alcohol, wherein the amount of (B) is 0.3 to 3 parts by weight based on one part by weight of (A) and the amount of (C) is 0.1 to 3 parts by weight based on one part by weight of the total amount of (A) and (B).

The highly polar oil used in the present invention refers to an oily substance which has the value of the inorganic character in the range of 115 to 500, and which has the number of carbon atoms in the range of 9 to 19. Preferred examples of the highly polar oil to satisfy such conditions are triethyl citrate, triacetin, piperonyl butoxide, dimethyl phthalate, diethyl phthalate, dibutyl phthalate, dioctyl phthalate and the like.

The amount of the highly polar oil is 1 to 50 parts by weight based on one part by weight of the highly polar and fat-soluble drug, preferably 1 to 20 parts by weight. In case of less than one part by weight, the highly polar and fat-soluble drug may be poorly dissolvable, while, in case of more than 50 parts by weight, the emulsion with minute particles may not easily obtainable.

In the present invention, it is necessary to contain the lowly polar oil for emulsification. The lowly polar oil to be used herein is an oily substance which has the value of the inorganic character of 200 or less, and has the number of carbon atoms of 20 or more. Preferred examples of the lowly polar oil are liquid paraffin, squalane, squalene, tocopherol, tocopherol acetate, tocopherol nicotinate, avocado oil, camellia oil, turtle oil, macadamia nut oil, corn oil, mink oil, olive oil, rapeseed oil, egg yolk oil, sesame oil, wheat germ oil, sasanqua oil, castor oil, safflower oil, cotton seed oil, soybean oil, peanut oil and medium chain fatty acid triglycerides such as tricaprilin. The amount of the lowly polar oil is 1 to 200 parts by weight based on one part of the highly polar and fat-soluble drug, preferably 10 to 50 parts by weight. In case of less than one part by weight, it may be difficult to emulsify, while, in case of more than 200 parts by weight, the highly polar and fat-soluble drug may be poorly dissolvable.

The value of the inorganic character in the present invention means the value which is calculated according to the method of Fujita indicated in Journal of Japanese Chemistry, vol. 11, 10, 719–725 (1957).

In the present invention, it is necessary to use the polyglycerol mono-fatty acid ester as an emulsifying agent because the emulsion having minute particles can not be obtained by using other emulsifying agents.

Preferred polyglycerol mono-fatty acid esters are those in which the glycerol polymerization grade is 5 or more, the number of carbon atoms of the fatty acid is in the range of 10 to 22 and the HLB is 12 or more. Among these polyglycerol mono-fatty acid esters, especially preferable ones are decaglycerol monostearate, decaglycerol monooleate, decaglycerol monopalmitate, decaglycerol monomyristate, decaglycerol monolaurate, hexaglycerol monomyristate or hexaglycerol monolaurate.

The amount of polyglycerol mono-fatty acid ester is in the range of 0.3 to 3 parts by weight based on one part by weight of the total amount of the oil phase (the highly polar and fat-soluble drug, the highly polar oil and the lowly polar oil), preferably 0.4 to 2 parts by weight. In case of less than 0.3 part by weight, the particle size may be increased, while, in case of more than 3 parts by weight, the internal preparation obtained thereby may cause bad taste.

In the present invention, it is essential to contain a water-soluble polyhydric alcohol for preparing the microemulsion.

Examples of the water-soluble polyhydric alcohol to be used in the present invention are ethylene glycol, propylene glycol, 1,3-butylene glycol, 1,4-butylene glycol, dipropylene glycol, polypropylene glycol, glycerol, diglycerol, polyglycerol, polyethylene glycol, erythritol, xylytol, sorbitol, maltitol, lactitol, mannitol, trehalose, sugar alcohol derived from digestion product of starch and the like. Among these water-soluble polyhydric alcohols, especially preferred ones are glycerol, diglycerol, polyglycerol and sorbitol. These water-soluble polyhydric alcohols are usually used in the form of a hydrous product. In this case, the weight ratio of the water-soluble polyhydric alcohol and water is preferably in the range of 95:5 to 50:50, and especially 90:10 to 55:45.

The amount of the water-soluble polyhydric alcohol to be used in the present invention is from 0.1 to 3 parts by weight based on one part by weight of the total amount of the oil phase and the polyglycerol mono-fatty acid ester, preferably 0.2 to 2 parts by weight.

In the present invention, the combination ratio of the oil phase, the polyglycerol mono-fatty acid ester and the water-soluble polyhydric alcohol is important, when the combination ratio is out of the range of the present invention, the microemulsion can not be obtained though the same components are used.

The highly polar and fat-soluble drug in the present invention refers to drugs having the value which is obtained by dividing the value of the inorganic character of the compound by the number of the carbon atoms contained in the compound molecule is 11 or more. The polarity of the drug can not be defined by only the value of the inorganic character, but gives generality by dividing by the number of the carbon atoms.

Examples of such highly polar and fat-soluble drug are fat-soluble vitamins such as riboflavine (the inorganic character/the number of carbon atoms=58.8) riboflavine tetrabutyrate (28.5) or bisibutiamine (O,O'-diisobutyrylthiamine disulfide) (25.0), aldioxa (276.3), proglumide (31.4), sulpiride (36.3), cimetidine (44.2), bergenin (50.4), sofalcone (11.5), bisoxatin acetate (16.0), aluminum flufenamate (28.5), salicylosalicylic acid (sasapyline) (24.3), ketophenylbutazone (26.1), glafenine (25.5), bucolome (34.6), feprazone (22.1), tolfenamic acid (18.6), acemetacin (24.5), diflunisal (22.3), timiperone (17.0), etizolam (20.9), oxaprozin (15.8), dimenhydrinate (28.3), thiethylperazine (16.2), chlorzoxazone (36.4), phenprobamate (23.5), carisoprodol (36.7), chlorphenesin carbamate (36.5), chlorinezanone (36.8), mezuitazine (14.3), mebhydrolin napadisylate (22.5), clemizole hydrochloride (16.1), clemastine fumarate (21.0), diisobutylaminobenzoyloxypropylthcophyline (29.8), hydrochlorothiazide (83.6), bendroflumethiazide (40.0), hydroflumethiazide (73.8), polythiazide (56.4), methyclothiazide (66.1), trichlormethiazide (75.6), cyclopenthiazide (45.8), cyclothiazide (43.2), benzthiazide (41.3), benzylhydrochlorothiazide (42.9), ethiazide (65.0), penflutiazide (45.4), spironolactone (15.9), triamterene (47.1), ethacrynic acid (20.9), chiortalidone (42.1), mefruside (41.2), clorexolone (34.6), tripamide (31.6), metolazone (35.0), rescinnamine (14.3), methoxerpidine (15.2), syrosingopine (16.0), mebutamate (44.0), meticrane (43.5), prazosin hydrochloride (29.5), nifedipine (17.1), etafenone hydrochloride (24.5), efloxate (12.6), hepronicate (15.5), simfibrate (11.3), nicomol (17.9), pyridinol carbamate (47.7), alprostadil (19.0), rutin (51.9), nicardipine hydrochloride (14.4), noscapine (12.7), hexoprenaline sulfate (35.0), bitolterol mesilate (12.0) and the like. Among them, the application of riboflavine or riboflavine tetrabutyrate to the present invention is especially effective in view of the stability of the drug.

The microemulsion of the present invention can be prepared by the following method. That is, the highly polar and fat-soluble drug is dissolved in the highly polar oil, mixed with the lowly polar oil and dissolved homogeneously to give the oil phase. The oil phase and a polyglycerol mono-fatty acid ester are mixed at an ordinary temperature or under heating and dissolved homogeneously. After the temperature is returned to the room temperature, a water-soluble polyhydric alcohol is gradually added to the solution with stirring to give a gel. The resulting gel is diluted with water, thereby there is obtained an O/W-type microemulsion with minute particles which contains the highly polar and fat-soluble drug.

The thus obtained microemulsion of the present invention, while containing the highly polar and fat-soluble drug, has a small average particle size of 50 to 300 nm, and it is remarkably stable for a long period of time even in an aqueous solution of pH 2.5 to 5 which is unstable in case of an ordinary emulsion, or even in an aqueous solution wherein the concentration of an ionic substance is 0.1 to 5% by weight. The ionic substance herein is a substance which forms an ion in an aqueous solution, and examples thereof are inorganic salts, or salts of organic acids with alkaline metals or alkaline earth metals.

It is known that, when the particle size of the emulsion is reduced, the contacting area of the particle of the emulsion with the aqueous phase is increased, thereby the stability of the drug in the emulsion is ordinarily affected. However, the microemulsion of the present invention ensures the stability of the drug in the emulsion in spite of the small particle size.

The microemulsion of the present invention may optionally contain the components to be ordinarily used in liquid preparations, such as other drugs, sweetening agents, pH conditioners, preservatives, perfumes, coloring agents, thickeners, chelating agents, ethanol or the like.

BEST MODE OF CARRYING OUT THE INVENTION

The present invention is illustrated in more detail by the following examples, manufacturing examples and experiments. The particle sizes described herein were the average particle sizes measured by using the dynamic light scattering method, specifically using NICOMP Model 370 (manufactured by HIAC/ROYCO).

EXAMPLE 1

In 6.25 g of triethyl citrate was dissolved 1.25 g of riboflavine tetrabutyrate, and then 50 g of tocopherol acetate was added thereto and mixed homogeneously. To the mixture were added 20 g of decaglycerol monomyristate (HLB 14) and 20 g of decaglycerol monostearate (HLB 15), and the whole mixture was mixed and dissolved at 60–70° C. The temperature was returned to room temperature, then 20 ml of 85% aqueous glycerol solution was added with stirring to give a gel, to which was then added purified water to make up to the total volume of 500 ml, thereby there was obtained a homogenous microemulsion having a particle size of 100 nm.

MANUFACTURING EXAMPLE 1

To 1 ml of the microemulsion obtained in Example 1 were added 1 g of taurine, 0.01 g of pyridoxine hydrochloride, 0.02 g of nicotinamide, 0.01 g of panthenol, 0.1 g of citric acid, 0.1 g of malic acid, 6 g of sucrose, 0.03 g of sodium benzoate and a slight amount of perfume, and the mixture was adjusted to pH 4.5 with 10% sodium hydroxide solution and made up to the total volume of 50 ml with purified water, thereby there was obtained a liquid preparation.

EXAMPLE 2

In 9.75 g of triacetine was dissolved 1.25 g of riboflavine, and then 50 g of tocopherol acetate was added thereto and mixed homogeneously. To the mixture were added 15 g of decaglycerol monopalmitate (HLB 14) and 20 g of decaglycerol monostearate (HLB 15), and the whole mixture was mixed and dissolved at 60–70° C. The temperature was returned to room temperature, then 30 ml of 85% aqueous glycerol solution was added with stirring to give a gel, to which was then added purified water to make up to the total volume of 500 ml, thereby there was obtained a homogenous micro-emulsion having a particle size of 120 nm.

MANUFACTURING EXAMPLE 2

To 1 ml of the microemulsion obtained in Example 2 were added 1 g of taurine, 0.01 g of pyridoxine hydrochloride, 0.02 g of nicotinamide, 0.1 g of inositol, 0.05 g of anhydrous caffeine, 0.2 g of citric acid, 6.5 g of sucrose, 0.03 g of sodium benzoate and a slight amount of perfume, and the mixture was adjusted to pH 4.0 with 10% sodium hydroxide solution and made up to the total volume of 50 ml with purified water, thereby there was obtained a liquid preparation.

EXAMPLE 3

In 5 g of triethyl citrate and 5 g of dibutyl phthalate was dissolved 1.25 g of riboflavine tetrabutyrate, and then 25 g of tocopherol acetate and 20 g of soybean oil were added thereto and mixed homogeneously. To the mixture were added 20 g of decaglycerol monomyristate (HLB 14) and 25 g of decaglycerol monostearate (HLB 15), and the whole mixture was mixed and dissolved at 60–70° C. The temperature was returned to room temperature, then 25 ml 10 of 85% aqueous glycerol solution was added with stirring to give a gel, to which was then added purified water to make up to the total volume of 500 ml, thereby there was obtained a homogenous micro-emulsion having a particle size of 150 nm.

MANUFACTURING EXAMPLE 3

To 1 ml of the microemulsion obtained in Example 3 were added 1 g of taurine, 0.01 g of pyridoxine hydrochloride, 0.02 g of nicotinamide, 0.1 g of inositol, 0.05 g of anhydrous caffeine, 0.3 g of citric acid, 6.5 g of sucrose, 0.03 g of sodium benzoate and a slight amount of perfume, and the mixture was adjusted to pH 3.5 with 10 % sodium hydroxide solution and made up to the total volume of 50 ml with purified water, thereby there was obtained a liquid preparation.

EXAMPLE 4

In 12.5 g of triethyl citrate was dissolved 2.5 g of riboflavine tetrabutyrate, and then 1 g of tocopherol and 50 g of tocopherol acetate were added thereto and mixed homogeneously. To the mixture were added 5 g of decaglycerol monolaurate (HLB 15.5), 20 g of decaglycerol monomyristate (HLB 14) and 20 g of decaglycerol monostearate (HLB 15), and the whole mixture was mixed and dissolved at 60–70° C. The temperature was returned to room temperature, then 25 ml of 85% aqueous glycerol solution was added with stirring to give a gel, to which was then added purified water to make up to the total volume of 500 ml, thereby there was obtained a homogenous microemulsion having a particle size of 130 nm.

MANUFACTURING EXAMPLE 4

There were mixed 1 ml of the microemulsion obtained in Example 4, 1.5 g of taurine, 0.005 g of thiamine nitrate, 0.005 g of pyridoxine hydrochloride, 0.02 g of nicotinamide, 0.1 g of inositol, 0.05 g of anhydrous caffeine, 0.05 g of ginseng extract, 0.2 g of royal jelly, 0.05 ml of stag horn tincture, 0.4 g of citric acid, 7.5 g of sucrose, 0.03 g of sodium benzoate and a slight amount of perfume, and then the mixture was adjusted to pH 3.0 with 10% sodium hydroxide solution and made up to the total volume of 50 ml with purified water, thereby there was obtained a liquid preparation.

EXAMPLE 5

In 25 g of triethyl citrate was dissolved 20 g of bisibutiamine, and then 50 g of tocopherol acetate was added thereto and mixed homogeneously. To the mixture were added 20 g of decaglycerol monomyristate (HLB 14) and 20 g of decaglycerol monostearate (HLB 15), and the whole mixture was mixed and dissolved at 60–70° C. The temperature was returned to room temperature, then 20 ml of 85% aqueous glycerol solution was added with stirring to give a gel, to which was then added purified water to make up to the total volume of 500 ml, thereby there was obtained a homogenous microemulsion having a particle size of 150 nm.

MANUFACTURING EXAMPLE 5

To 1 ml of the microemulsion obtained in Example 5 were added 1.5 g of taurine, 0.005 g of pyridoxine hydrochloride, 0.02 g of nicotinamide, 0.1 g of inositol, 0.05 g of anhydrous caffeine, 0.05 g of ginseng extract, 0.2 g of royal jelly, 0.05 ml of stag horn tincture, 0.4 g of citric acid, 7.5 g of sucrose, 0.03 g of sodium benzoate and a slight amount of perfume, and the mixture was adjusted to pH 3.0 with 10% sodium hydroxide solution and made up to the total volume of 50 ml with purified water, thereby there was obtained a liquid preparation.

COMPARATIVE EXAMPLE 1

No Use of Lowly Polar Oil

Following the same manner as in Example 1 using the same formulation as in Example 1 except for no use of tocopherol and use of triethyl citrate in the increased amount to 10 g, there was obtained an emulsion having a particle size of 950 nm.

Following the same manner as in Manufacturing Example 1 using the resulting emulsion, there was a comparative liquid preparation.

COMPARATIVE EXAMPLE 2

No Use of Highly Polar Oil

In 10 ml of ethanol was dissolved 1.25 g of riboflavine tetrabutyrate, and then 60 g of tricaprilin and 50 g of soybean oil were added thereto and mixed homogeneously. To the mixture were added 10 g of decaglycerol monomyristate (HLB 14) and 10 g of decaglycerol monostearate (HLB 15), and the whole mixture was mixed and dissolved at 60–70° C. The temperature was returned to room temperature, then 45 ml of 85% aqueous glycerol solution was added with stirring to give an emulsion, to which was then added purified water to make up to the total volume of 500 ml, thereby there was obtained an emulsion having a particle size of 1100 nm.

Following the same manner as in Manufacturing Example 1 using 1 ml of the resulting emulsion, there was obtained a comparative liquid preparation.

COMPARATIVE EXAMPLE 3

Method for Dissolving by Surface Active Agent

At about 80° C., 0.025 g of riboflavine tetrabutyrate and 2.0 g of polyoxyethylene hydrogenated castor oil (HCO-60) were dissolved on a water bath with stirring, and then purified water (about 80° C.) was added thereto. After conformation of dissolution, the solution was cooled, thereby there was obtained a liquid preparation of riboflavine tetrabutyrate, to which were then added 1 g of taurine, 0.01 g of pyridoxine hydrochloride, 0.02 g of nicotinamide, 0.01 g of panthenol, 0.1 g of citric acid, 0.1 g of malic acid, 6 g of sucrose, 0.03 g of sodium benzoate and a slight amount of perfume, and the mixture was adjusted to pH 4.5 with 10% sodium hydroxide solution and made up to the total volume of 50 ml with purified water, thereby there was obtained a comparative liquid preparation.

TEST EXAMPLE 1

The liquid preparations of Examples 1 to 5 and Comparative Examples 1 to 3 were each filled into a 50 ml-coloring glass bottle, and after fitting with a stopper, sterilized with heating. As a result of a macroscopic observation of the properties, no change was found in Examples 1 to 5 and Comparative Example 3, and the isolation of the oil and water by sterilization with heating was found in Comparative Examples 1 and 2.

TEST EXAMPLE 2

The liquid preparations of Examples 1 to 5 were each stored at 40° C. for 3 months, after which the properties of the emulsions thereof were observed macroscopically. As a result, no change was found in any liquid preparations when compared with those just produced.

TEST EXAMPLE 3

The preparations of Example 1 and Comparative Example 3 were each stored in the dark at 40° C. for 3 months, after which the residual riboflavine tetrabutyrate in the preparation was quantified by high perfomance liquid chromatography. As a result, the residual ratio of riboflavine tetrabutyrate of Example 1 is 95.7%, and the residual ratio of riboflavine tetrabutyrate of Comparative Example 3 is 75.6%.

INDUSTRIAL APPLICABILITY

The present invention makes it possible to make a microemulsion which, while containing the highly polar and fat-soluble drug, is remarkably stable in an aqueous solution having a high concentration of the ionic substance or in acidic region, thereby the microemulsion of the present invention can be applied into aqueous preparations in the fields of pharmaceutical, foods and cosmetics.

What is claimed is:

1. A microemulsion containing (A) a highly polar and fat-soluble oil drug, a highly polar oil and a lowly polar oil, (B) a polyglycerol mono-fatty acid ester and (C) a water-soluble polyhydric alcohol, wherein the amount of (B) is 0.3 to 3 parts by weight based on one part by weight of (A) and the amount of (C) is 0.1 to 3 parts by weight based on one part by weight of the total amount of (A) and (B).

2. The microemulsion according to claim 1 wherein the highly polar oil is an oily substance which has the value of the inorganic character in the range of 115 to 500, and which has the number of carbon atoms in the range of 9 to 19.

3. The microemulsion according to claim 1 wherein the highly polar oil is selected from triethyl citrate, triacetin, piperonal butoxide, dimethyl phthalate, diethyl phthalate, dibutyl phthalate or dioctyl phthalate.

4. The microemulsion according to claim 1 wherein the polyglycerol mono-fatty acid ester is an ester of a polyglycerol having the polyglycerol polymerization grade of 5 or more with a fatty acid having the number of carbon atoms of 10 to 22 wherein the HLB is 12 or more.

5. The microemulsion according to claim 1 wherein the polyglycerol mono-fatty acid ester is selected from decaglycerol monostearate, decaglycerol monooleate, decaglycerol monopalmitate, decaglycerol monomyristate, decaglycerol monolaurate, hexaglycerol monomyristate or hexaglycerol monolaurate.

6. The microemulsion according to claim 1 wherein the water-soluble polyhydric alcohol is selected from glycerol, diglycerol, polyglycerol or sorbitol.

7. The microemulsion according to claim 1 wherein the lowly polar oil is an oily substance which has the value of the inorganic character of 200 or less, and which has the number of carbon atoms of 20 or more.

8. The microemulsion according to claim 1 wherein the lowly polar oil is selected from liquid paraffin, squalane, squalene, tocopherol, tocopherol acetate, tocopherol nicotinate, avocado oil, camellia oil, turtle oil, macadamia nut oil, corn oil, mink oil, olive oil, rapeseed oil, egg yolk oil, sesame oil, wheat germ oil, sasanqua oil, castor oil, safflower oil, cotton seed oil, soybean oil, peanut oil or tricaprilin.

9. The microemulsion according to claim 1 wherein the highly polar and fat-soluble drug is a drug having the value which is obtained by dividing the value of the inorganic character of the compound by the number of the carbon atoms is 11 or more.

10. The microemulsion according to claim 1 wherein the highly polar and fat-soluble drug is riboflavine tetrabutyrate.

11. The microemulsion according to claim 1 wherein the amount of the highly polar oil is 1 to 50 parts by weight based on one part by weight of the highly polar and fat-soluble drug.

12. The microemulsion according to claim 1 wherein an average particle size of the emulsion is 50 to 300 nm.

13. The microemulsion according to claim 1 wherein said microemulsion is an oil-in-water emulsion comprising a discontinuous oil phase containing (A), said discontinuous phase being dispersed in a continuous aqueous phase.

* * * * *